United States Patent
Huang et al.

(10) Patent No.: US 9,789,207 B1
(45) Date of Patent: Oct. 17, 2017

(54) METHOD OF FABRICATING [F-18]FEONM

(71) Applicant: Institute of Nuclear Energy Research, Atomic Energy Council, Executive Yuan, R.O.C., Taoyuan (TW)

(72) Inventors: Li-Yuan Huang, Taoyuan (TW); Yean-Hung Tu, Taoyung (TW); Jenn-Tzong Chen, Taipei (TW); Chyng-Yann Shiue, Taipei (TW)

(73) Assignee: INSTITUTE OF NUCLEAR ENERGY RESEARCH, ATOMIC ENERGY COUNCIL, Executive Yuan, R.O.C., Lungtan, Taoyuan (TW)

( * ) Notice: Subject to any disclaimer, the term of this patent is extended or adjusted under 35 U.S.C. 154(b) by 19 days.

(21) Appl. No.: 15/184,129

(22) Filed: Jun. 16, 2016

(51) Int. Cl.
*A61K 49/00* (2006.01)
*C07C 255/09* (2006.01)

(52) U.S. Cl.
CPC ........ *A61K 49/0052* (2013.01); *C07C 255/09* (2013.01)

(58) Field of Classification Search
None
See application file for complete search history.

(56) References Cited

U.S. PATENT DOCUMENTS

| | | | |
|---|---|---|---|
| 9,186,423 B1* | 11/2015 | Lin | C07C 255/42 |
| 2013/0315826 A1* | 11/2013 | Mukherjee | A61K 51/04 424/1.89 |

* cited by examiner

*Primary Examiner* — Clinton Brooks
(74) *Attorney, Agent, or Firm* — Jackson IPG PLLC; Demian K. Jackson

(57) ABSTRACT

A PET imaging agent is made, by at first, washing out fluoride ions (F-18) adhered on an ion exchange resin to a reaction vessel with potassium carbonate/Kryptofix 2.2.2 in acetonitrile-water. After processing the first azeotropic distillation with helium while water is removed, the temperature is cooled down. Then, acetonitrile is added to the reaction vessel to be heated up. After processing the second azeotropic distillation with helium while water is removed, the temperature is cooled down and excess water is extracted. A precursor is then added to the reaction vessel to be heated up for processing a fluorination reaction. The reaction mixture obtained after the fluorination reaction is cooled down to be flown through a solid-phase extraction column with waste drained into a waste tank. Then, ethanol is used to wash out a product, i.e. [F-18]FEONM, adsorbed by the column, to be collected in a collection vial.

4 Claims, 2 Drawing Sheets

METHOD OF FABRICATING [F-18]FEONM

TECHNICAL FIELD OF THE INVENTION

Figure 1:
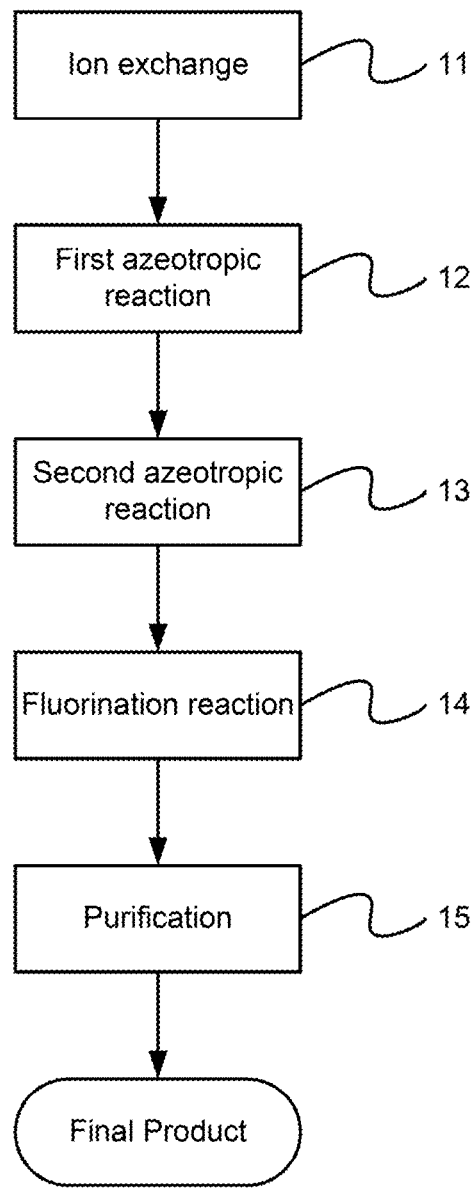

The present invention relates to fluorine-18 (F-18) FEONM; more particularly, relates to easily producing a PET imaging agent for the diagnosis of Alzheimer's disease with time saved and production efficiency improved.

DESCRIPTION OF THE RELATED ARTS

Alzheimer's disease has become a serious health and socio-economic problem. There are a lot of researches and developments for techniques and methods of early detection and effective treatment.

Positron emission tomography (PET) is a nuclear medicine diagnostic technology rapidly developed in recent years. The use of radionuclide fluorine-18 ($^{18}$F) has a relatively long half-life ($t_{1/2}$=110 min) to allow more adequate time for drug labeling and image study. Its hydrogen-like characteristic does not cause significant change on spatial structure and biological activity of the labeled molecule. Thus, fluorine-18 is widely used as a radionuclide for labeling receptor ligand, glucose, amino acids, fatty acids, nucleosides, etc. PET is used to study non-invasively glucose metabolism, protein synthesis and activities of neurotransmitter function, for diagnosing cardiovascular, neurological and psychiatric disorders, cancers, and for monitoring the efficacy of the treatments. Labeling with fluorine-18 and screening appropriate labeled drugs are focused in current researches.

Fluorine-18 deoxyglucose (2-[$^{18}$F]Fluoro-2-Deoxy-D-glucose, [$^{18}$F]-FDG) is the most widely used PET imaging agent in clinic, whose metabolic trapping in tissues intracellularly is used for evaluating diagnoses and treatments of a variety of diseases in neurology, cardiology, psychiatry and oncology. However, its diagnosis is relatively non-specific and does not fully meet clinical needs. Thus, various more specific PET imaging agents are developed.

However, even many researchers try to use fluorine-18 for labeling to obtain clear imaging results in animal, labeling still has many shortcomings currently. The main disadvantages are the long time for labeling, including reaction time; and high-performance liquid chromatography (HPLC) is required for isolating and purifying the products.

Hence, the prior arts do not fulfill all users' requests on actual use.

SUMMARY OF THE INVENTION

The main purpose of the present invention is to easily produce a PET imaging agent for the diagnosis of Alzheimer's disease with time saved and production efficiency improved.

To achieve the above mentioned purpose, the present invention is a method of fabricating [F-18]FEONM, comprising steps of: (a) washing out fluoride ions, being adhered on an ion exchange resin, with potassium carbonate/Kryptofix 2.2.2 in acetonitrile-water into a reaction vessel; (b) heating the reaction vessel to a temperature of 75~115 Celsius degrees (° C.) with helium flowing through the reaction vessel to process a first azeotropic process with water to be excluded and then cooling the temperature down to 40~60°; (c) adding acetonitrile to the reaction vessel to be heated to a temperature of 75~115° C. with helium flowing through the reaction vessel to process a second azeotropic process with water to be excluded and then cooling the temperature down to 40~60° C.; (d) adding a precursor to the reaction vessel to be heated to a temperature of 90~130° C. to process a fluorination reaction for 10~20 minutes to obtain a reaction mixture; and (e) after the fluorination reaction, cooling a temperature of the reaction mixture down to 40~60° C. to be flown through a solid phase extraction column with waste drained into a waste tank and washing out a final product of [F-18]FEONM, being adhered on the column, with ethanol to be collected in a collection tank. Accordingly, a novel method of fabricating [F-18]FEONM is obtained.

BRIEF DESCRIPTION OF THE DRAWING(S)

Figure 2:
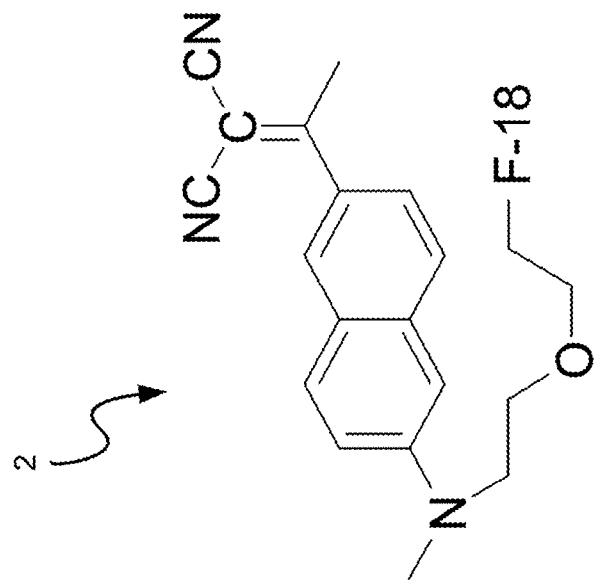
Figure 2:
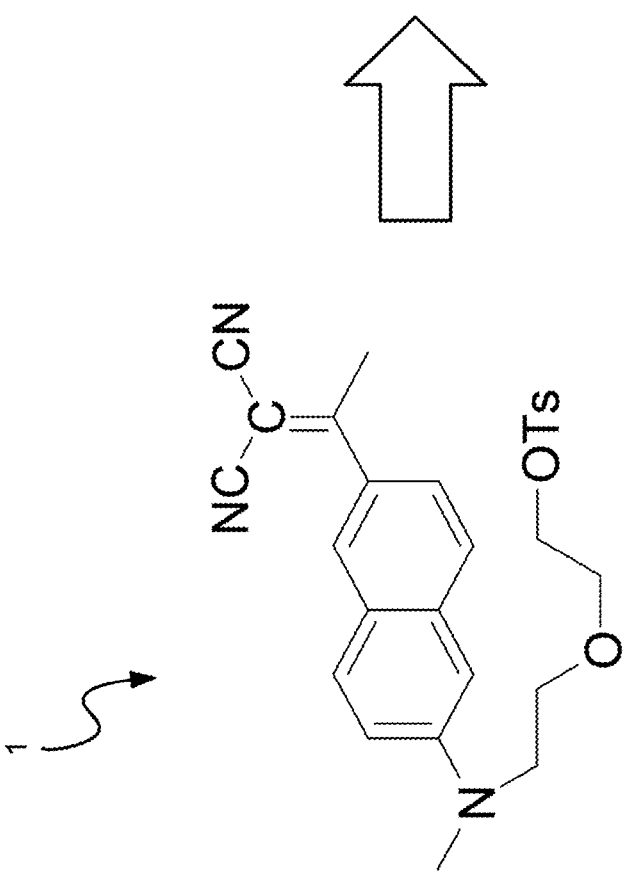

The present invention will be better understood from the following detailed description of the preferred embodiment(s) according to the present invention, taken in conjunction with the accompanying drawing(s), in which FIG. 1 is the flow view showing the preferred embodiment according to the present invention; and FIG. 2 is the view showing the fluorination reaction.

DESCRIPTION OF THE PREFERRED EMBODIMENT

The following description of the preferred embodiment is provided to understand the features and the structures of the present invention.

Please refer to FIG. 1 and FIG. 2, which are a flow view showing a preferred embodiment according to the present invention; and a view showing a fluorination reaction. As shown in the figures, the present invention is a method of fabricating [F-18]FEONM, comprising the following steps:

(a) Ion exchange 11: Fluoride ions (F-18) adhered on an ion exchange resin are washed out into a reaction vessel with potassium carbonate/Kryptofix 2.2.2 in acetonitrile-water.

(b) First azeotropic distillation 12: The reaction vessel that contains fluoride ions (F-18)/potassium carbonate/Kryptofix 2.2.2 in acetonitrile-water will be heated to a temperature of 95 celsius degrees (° C.). After the first azeotropic process is processed with helium and water is excluded, the temperature is cooled down to 50° C.

(c) Second azeotropic distillation 13: Acetonitrile is added to said reaction vessel to be heated to a temperature of 95 Celsius degrees (° C.). After the second azeotropic distillation is processed with helium and water is excluded, the temperature is cooled down to 50° C.

(d) Fluoridation reaction 14: A precursor 1 is added to said reaction vessel to be heated to a temperature of 110° C. to process a fluorination reaction for 15 minutes to obtain a reaction mixture. Therein, the precursor 1 has a formula as follows:

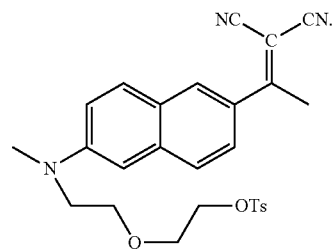 [SMILES: CC(=C(C#N)C#N)c1ccc2cc(N(C)CCOCCOS(=O)(=O)c3ccc(C)cc3)ccc2c1]

(e) Purification 15: A temperature of the reaction mixture obtained after the fluorination reaction is cooled down to 50°

C., the reaction mixture will be passed through a solid phase extraction column for processing solid phase extraction (SPE) with waste drained into a waste tank. Then, ethanol is obtained to wash out a final product of [F-18]FEONM, being adhered on the column, to be collected in a collection vial. Therein, the final product of [F-18]FEONM has a formula as follows:

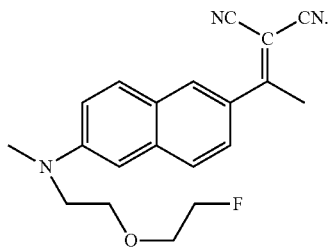 [SMILES: CC(=C(C#N)C#N)c1ccc2cc(N(C)CCOCCF)ccc2c1]

Thus, a novel method of fabricating [F-18]FEONM is obtained.

To sum up, the present invention is a method of fabricating [F-18]FEONM, where [F-18]FEONM, a PET imaging agent for the diagnosis of Alzheimer's disease, can be easily produced with time saved and production efficiency improved.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating FEONM, 2-(1-{6-[(2-2'-[F-18] Fluoroethoxyethyl)(methyl)amino]-2-naphthyl}ethylidene) malononitrile ([F-18]FEONM), comprising steps of:
    (a) washing out fluoride ions (F-18), being adhered on an ion exchange resin, with potassium carbonate/2.2.2 cryptand in acetonitrile-water into a reaction vessel;
    (b) heating said reaction vessel to be heated to a temperature of 75-115 celsius degrees (° C.), cooling said temperature down to 40-60° C. and excluding water after processing a first azeotropic distillation with helium;
    (c) adding acetonitrile to said reaction vessel to be heated to a temperature of 75-115° C., cooling said temperature down to 40-60° C. and excluding water after processing a second azeotropic distillation with helium;
    (d) adding a precursor to said reaction vessel to be heated to a temperature of 90-130° C. to process a fluorination reaction for 10-20 minutes to obtain a reaction mixture; and
    (e) after said fluorination reaction, cooling down a temperature of said reaction mixture to 40-60° C. followed by flowing said reaction mixture through a solid phase extraction column with waste drained into a waste tank and washing out a final product of [F-18]FEONM, being adhered on said column, with ethanol to be collected in a collection vial.

2. The method according to claim 1,
    wherein, in step (b), said fluorinating agent is fluoride ions (F-18)/potassium carbonate/2.2.2 cryptand.

3. The method according to claim 1,
    wherein, in step (d), said precursor has a formula as follows:

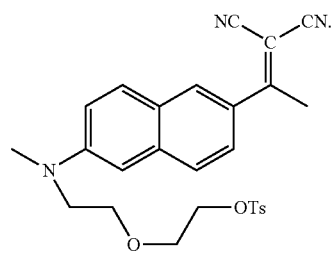 [SMILES: CC(=C(C#N)C#N)c1ccc2cc(N(C)CCOCCOS(=O)(=O)c3ccc(C)cc3)ccc2c1]

4. The method according to claim 1,
    wherein, in step (e), said final product of [F-18]FEONM has a formula as follows:

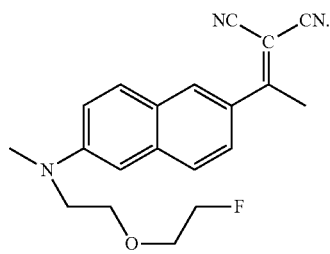 [SMILES: CC(=C(C#N)C#N)c1ccc2cc(N(C)CCOCCF)ccc2c1]

* * * * *